United States Patent
O'Shea et al.

(10) Patent No.: US 7,070,972 B1
(45) Date of Patent: Jul. 4, 2006

(54) JANUS FAMILY KINASES AND IDENTIFICATION OF IMMUNE MODULATORS

(75) Inventors: John J. O'Shea, Silver Spring, MD (US); Warren J. Leonard, Bethesda, MD (US); James A. Johnston, Middletown, MD (US); Sarah M. Russell, Kensington, MD (US); Daniel W. McVicar, Charles Town, WV (US); Masaru Kawamura, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/373,934

(22) Filed: Jan. 13, 1995

(51) Int. Cl.
*C12N 9/12* (2006.01)
*C12N 9/10* (2006.01)
*C07K 14/435* (2006.01)

(52) U.S. Cl. .................. 435/194; 435/193; 530/350
(58) Field of Classification Search ............... 530/350, 530/395; 435/183, 212, 194, 193
See application file for complete search history.

(56) References Cited

U.S. PATENT DOCUMENTS

| 5,124,251 | A | | 6/1992 | Lanier et al. |
| 5,262,522 | A | | 11/1993 | Gearing |
| 5,283,354 | A | | 2/1994 | Lemischka |
| 5,705,625 | A | * | 1/1998 | Civin et al. ............... 536/23.5 |
| 5,916,792 | A | | 6/1999 | Civin et al. |
| 6,136,595 | A | | 10/2000 | Ihle et al. ............... 435/320.1 |

FOREIGN PATENT DOCUMENTS

WO 9400469 1/1994

OTHER PUBLICATIONS

Lai et al., Blood, vol. 84 (10 Suppl 1), 294A, 1994.*
Safford et al., Blood, vol. 84 (10 Suppl 1), 122A, 1994.*
Zeng et al., FEBS Letters, 353:289-293, 1994.*
Asao et al., FEBS Letters, 351:201-206, 1994.*
Takahashi et al., FEBS Letters, 342:124-128, 1994.*
Rane et al., Oncogene, 9:2415-2423, 1994.*
Miyazaki et al., Science, 266:1045-1047, 1994.*
Beadling et al., EMBO J., 13:5605-5615, 1994.*
Kirkew et al., J. Biol. Chem., 268:22765-22770, 1993.*
Hunter, Tony; Nature, vol. 366, Nov. 11, 1993; pp. 114-116; "Cytokine Connections".
McVicar, et al.; Oncogene, Jul. 1994 9(7), pp. 2037-2044; "Molecular Cloing of lsk, a carboxyl-terminal src kinase (csk) related gene, expressed in leukocytes".

Kawamura, et al.; Proc.Natl.Acad.Sci.USA, vol. 91, pp. 6374-6378, Jul. 1994; "Molecular cloing of L-JAK, a Janus family protein-tyrosine kinase expressed in natural killer cells and activated leukocytes".
Russell, et al.; "Interaction of Interleukin-2 Receptor β chain and common Chain with JAK1 and JAK3, respectively:defective Jak3 Association in X-linked Severe Combined Immunodeficiency". AIDS Res. and Human Retrovir. vol. 10 (Suppl 3), 1994, 573.
Gnarra, et al., Proc.Natl.Acad.Sci.USA; vol. 87, pp. 3440-3444, May 1990, Immunology; "Human interleukin 2 receptor β-chain gene: Chromosomal localization and identification of 5' regulatory sequences".
Russell, et al.; Science, vol. 262, Dec. 17, 1993; pp. 1880-1883; "Interleukin-2 receptor γ Chain: A functional Compnent of the Interleukin-4 receptor".
Noguchi, et al. ; The Journal of Biological Chemistry; vol. 268, No. 18, Jun. 25, 1993, pp. 13601-13608; "Characterization of the Human Interleukin-2 Receptor γ Chain Gene".
Russell, et al.; Science, vol. 266, Nov. 11, 1994; pp. 1042-1045; "Interaction of IL-2Rβ and γ chains with Jak1 and Jak3: Implications for XSCID and XCID".
Takebe, et al.; Molecular and Cellular Biology, Jan. 1988, pp. 466-472; "Sr Promoter: an Efficient and Versatile Mammalian cDNA Expression System Composed of the Simian Virus 40 Early Promoter and the R-U5 Segment of Human T-Cell Leukemia Virus Type 1 Long Terminal Repeat".
Nakamura et al.; Nature, vol. 369; May 26, 1994, pp. 330-333; "Heterodimerization of the IL-2 receptor β and γ chain ccytoplasmic domains is required for signaling".
Cance, et al.; INt.J. Cancer: 54, 571-577 (1993); "Novel Protein Kinases expressed in human breast cancer".
Johnston, et al.; Nature, vol. 370, Jul. 14, 1994; pp. 151-153; "Phosphorylation and activation of the Jak-3 Janus Kinase in response to Interleukin-2".
Withuhn, et al.; Nature, vol. 370, Jul. 14, 1994; pp. 153-157; "Involvement of the JAk-3 Janus kinase in signaling by interleukins 2 and 4 in lymphoid and myeloid cells".
Sanchez, et al.; Proc.Natl.Acad.Sci.USA, vol. 91, pp. 1819-1823, Mar. 1994, Neurobiology; "Multiple tyrosine protein kinases in rat hippocampal neurons: Isolation of Ptk-3, a receptor expressed in proliferative zones of the developing brain".

(Continued)

*Primary Examiner*—Ronald B. Schwadron
(74) *Attorney, Agent, or Firm*—Knobbe, Martens, Olson & Bear, LLP

(57) ABSTRACT

An isolated polynucleotide encodes JAK-3 protein. JAK-3 protein is a protein tyrosine kinase having a molecular weight of approximately 125 kDa which has tandem nonidentical catalytic domains, lacks SH2 or SH3 domains, and is expressed in NK cells and stimulated or transformed T cells, but not in resting T cells. The protein itself and antibodies to this protein are also presented. Further, methods of identifying therapeutic agents for modulating the immune system make use of the foregoing.

1 Claim, No Drawings

OTHER PUBLICATIONS

Siliciano, et al.; Proc.Natl.Acad.Sci.USA, vol. 89, pp. 11194-11198; Dec. 1992; Biochemistry; "itk, a T-cell-specific thyrosine kinase gene inducible by interleukin 2".

Vitte-Mony, et al.; 1994 Elsevier Science Ltd, Mol. Immunol. Jun. 1994; pp. 623-632; "Signal Transduction of interleukin 2 in Human Natural Killer Cells: Involvement of the p56$^{lck}$ Tyrosine Kinase".

Sharon, et al.; Proc.Natl.Acad.Sci.USA; vol. 87, pp. 4869-4873, Jun. 1990, Immunology; "A 100-kilodalton protein is associated with the murine interleukin 2 receptor: Biochemical evidence that p100 is distinct from the α and β chains".

Bennett, et al.; The Journal of Biological Chemistry, vol. 269, No. 2, Issue of Jan. 14, pp. 1068-1074, 1994; "Identification and Characterization of a Novel Tyrosine Kinase from Megakaryocytes".

Stahl, et al.; Cell, vol. 74, pp. 587-590, August 27, 1993; "The Alphas, Betas, and kinases of Cytokine Receptor Complexes".

* cited by examiner

US 7,070,972 B1

JANUS FAMILY KINASES AND IDENTIFICATION OF IMMUNE MODULATORS

FIELD OF THE INVENTION

The present invention relates generally to the field of transmembrane signal transduction. More specifically, the invention relates to the components of multisubunit receptors for cytokines, and assays for detecting interactions between these components.

BACKGROUND OF THE INVENTION

Protein tyrosine kinases (PTK) are critical enzymes for receptor-mediated signal transduction in lymphocytes. Indeed, protein tyrosine phosphorylation is an early and requisite event in signaling for both multichain immune recognition receptors such as the T-cell antigen receptor (TCR) and cytokine receptors. Unlike growth factor receptors, neither the TCR nor the cytokine receptors have intrinsic PTK activity. Rather, they are coupled to nonreceptor tyrosine kinases. For example, the src family PTK, Lck and Fyn have been implicated in TCR-mediated signaling. The non-src family PTK Zap-70 has been shown to associate with the TCR upon activation. The src family PTK, Lck, Fyn and Lyn have also been implicated in Interleukin-2 (IL-2) receptor mediated signaling.

The Janus family kinases (JAKs) represent a recently described family of PTK. These kinases, called JAK-1, JAK-2 and Tyk-2, are structurally quite distinct in that they possess tandem nonidentical catalytic domains. These PTK are ubiquitously expressed and have been shown to participate in signaling by a number of cytokine and hormone receptors. These PTK are believed to exert their effects through tyrosyl phosphorylated transcription factors.

IL-2 is a T-cell lymphokine that both functions as a potent autocrine growth factor and activates other cells, including B-cells and natural killer (NK) cells. In addition, the interaction of IL-2 with high affinity IL-2 receptors regulates the magnitude and duration of the normal T-cell immune response.

High affinity IL-2 receptors comprise three receptor components, denoted the IL-2 receptor $\alpha$, $\beta$ and the common $\gamma$ ($\gamma_c$) chain. Interestingly, the $\gamma_c$ chain is a receptor component that is shared by the receptors for several of the interleukins. In the mechanism of IL-2 signal transduction, IL-2 binding induces heterodimerization of the cytoplasmic domains of $\beta$ and $\gamma_c$. This heterodimerization is required for IL-2 signaling.

While the IL-2 receptor is a multi-subunit complex that lacks intrinsic enzymatic activity, it is clear that protein tyrosine phosphorylation is an early biochemical step that follows ligand binding. Occupancy of the IL-2 receptor additionally stimulates alkalinization of T-cells via $Na^+/H^+$ exchange, activation of Ras, Raf and ERK1, induction of the fos, jun and myc proto-oncogenes, as well as induction of effector functions such as cytotoxicity and cellular proliferation.

SUMMARY OF THE INVENTION

One aspect of the invention provides an isolated polynucleotide encoding the JAK-3 protein. The JAK-3 protein is a protein tyrosine kinase that has a molecular weight of approximately 125 kDa. In addition, the JAK-3 protein is characterized by tandem non-identical catalytic domains. The JAK-3 protein lacks SH2 or SH3 domains, and is expressed in NK cells and stimulated or transformed T-cells, but not substantially expressed in resting T-cells. In a preferred embodiment, the isolated polynucleotide encoding the JAK-3 protein has the nucleotide sequence of SEQ ID NO:8.

A second aspect of the invention relates to an isolated JAK-3 protein. The JAK-3 protein is a protein tyrosine kinase having a molecular weight of approximately 125 kDa, has tandem non-identical catalytic domains, lacks SH2 or SH3 domains, and is expressed in NK cells and stimulated or transformed T-cells, but not substantially expressed in resting T-cells. In a preferred embodiment, the isolated JAK-3 protein has the polypeptide sequence of SEQ ID NO:9.

A third aspect of the invention relates to an antibody that is specific to JAK-3 protein. As described above, the JAK-3 protein is a protein tyrosine kinase having a molecular weight of approximately 125 kDa. The JAK-3 protein recognized by the claimed antibody has tandem non-identical catalytic domains, lacks SH2 or SH3 domains, and is expressed in NK cells and stimulated or transformed T-cells, but not substantially expressed in resting T-cells. In a preferred embodiment, the antibody that specifically recognizes the JAK-3 protein is polyclonal.

A fourth aspect of the invention provides a method of identifying an agent having immunomodulating activity. This method includes first determining the ability of the $\beta$ or $\gamma_c$ chain of the IL-2 receptor to physically associate with a Janus family kinase selected from the group consisting of JAK-1 and JAK-3 in the absence of a candidate immunomodulatory agent. A second step includes determining the ability of a chain of the IL-2 receptor to physically associate with a Janus family kinase in the presence of the candidate immunomodulating agent. If the candidate immnomodulating agent causes either a lesser or greater ability of the IL-2 receptor chain and the Janus family kinase to associate with each other, then such an ability will indicate that the candidate agent has immunomodulating activity. In a preferred embodiment, the two determining steps are performed in the presence of a cytokine compound. In a more preferred embodiment, the cytokine compound is a cytokine compound that binds to a receptor that includes the $\gamma_c$ chain. In yet a more preferred embodiment, the cytokine compound is selected from the group consisting of IL-2, IL-4, IL-7, IL-9 and IL-15. In another preferred embodiment, each of the determining steps includes immunoprecipitating a chain of the IL-2 receptor with an antibody that is specific to that chain, and then determining if the Janus family kinase coprecipitates with that receptor chain. According to this embodiment, the candidate agent can be a peptide fragment of the $\gamma_c$ chain of the IL-2 receptor.

A fifth aspect of the invention relates to a method of identifying a therapeutic agent for modulating the immune system. This method includes first isolating a Janus family kinase selected from the group consisting of JAK-1 and JAK-3. A subsequent step involves determining the ability of the kinase to phosphorylate a substrate in the absence of a candidate agent, and then determining the ability of the kinase to phosphorylate the substrate in the presence of the candidate agent. A decrease in the ability of the kinase to phosphorylate the substrate in the presence of the candidate agent indicates that said candidate agent is an immunosuppressive agent. Alternatively, a greater ability of the kinase to phosphorylate the substrate in the presence of the candidate agent indicates that said candidate agent is an immunoenhancing agent. In a preferred embodiment, the isolating step includes immunoprecipitating the Janus family kinase with an antibody specific to the Janus family kinase. In a more preferred embodiment, each of the determining steps includes first reacting the Janus family kinase with γ-labeled ATP to produce reaction products, and then separating the reaction products by electrophoresis and identifying the labeled products. In an even more preferred embodiment, each of the determining steps includes first reacting the Janus family kinase with ATP to produce reaction products, then separating the reaction products by electrophoresis, exposing the separated reaction products to a labeled antibody specific for phosphotyrosine, and finally identifying the reaction products that exhibit binding to the antibody.

DETAILED DESCRIPTION OF THE INVENTION

We have discovered that a novel protein tyrosine kinase (PTK), called JAK-3, has structural features characteristic of the Janus family of PTK. Unlike the three other members of this family, JAK-3 is only expressed in a narrow spectrum of cell types. Whereas JAK-1, JAK-2 and Tyk2 are broadly expressed, JAK-3 is the first Janus family member that exhibits limited tissue expression, or that is induced following cellular activation. In particular, JAK-3 was found to be predominantly expressed in activated human T lymphocytes and NK cells. We also have observed JAK-3 expression in IFN-γ activated human peripheral blood monocytes and B-cells. Based on this pattern of gene expression, we believe that the function of JAK-3 is related to important signaling pathways in these cell types. However, we acknowledge that JAK-3 could also be inducible in nonhematopoietic tissues by appropriate stimuli.

Herein we disclose that IL-2 can rapidly induce activation and tyrosine phosphorylation of JAK-3 in responsive cells. Additionally, we show that JAK-1, although less prominently tyrosine-phosphorylated, also is involved in IL-2 receptor signaling. The data presented below indicate that both JAK-3 and JAK-1 play important roles in lymphoid activation via the IL-2 receptor. Specifically, JAK-3 and JAK-1 associate with other components of the IL-2 receptor to form an activated receptor complex. Thus, agents that inhibit the interaction of either JAK-1 or JAK-3 with other components of the receptor are considered as candidates for immunomodulatory drugs. We contemplate that such immunomodulatory drugs can be either immunosuppressing or immunoenhancing.

More specifically, compounds that inhibit the interaction of JAK-1 with IL-2Rβ, or the interaction of JAK-3 with the $\gamma_c$ subunit of the IL-2 receptor complex are expected to inhibit IL-2 dependent signal transduction. These inhibitory compounds can act through mechanisms involving drug interaction with the kinase, or with the receptor substrate. In the first instance, the compound may interact with the kinase such that the kinase fails to phosphorylate the receptor chain. Alternatively, the inhibitor may act on the kinase such that it fails to autophosphorylate. According to another contemplated mechanism, the inhibitory compound may interact with one of the chains of a multisubunit receptor, so that interaction with the Janus family kinase is inhibited. Finally, we contemplate compounds which disrupt the binding between one receptor chain and the Janus family kinase that ordinarily binds to that receptor subunit.

The development of assays for identifying compounds that inhibit IL-2 dependent signalling represents an important step toward the discovery of novel immunomodulators. Compounds having inhibitor activity in such assays will be identified as potential therapeutics for the treatment of autoimmune diseases and transplant rejection. Autoimmune diseases anticipated as objects of therapy using drugs identified according to the assays disclosed herein include, but are not limited to, rheumatoid arthritis, psoriatic arthritis, lupus and vasculitis. Certain of the drugs identified according to the present invention are likely to be useful not only in the treatment of disorders resulting from inappropriate activation of the IL-2 receptor, but also from inappropriate activation of other cytokine receptors that share common subunits with the IL-2 receptor.

Our approach to the development of an assay for compounds that inhibit IL-2 dependent signalling stems from our understanding of the detailed structure of the IL-2 receptor complex. In particular, we have discovered that two different Janus family tyrosine kinases interact with different subunits of the IL-2 receptor. Binding of the JAKs to the receptor subunits represents a critical step in the cytokine signalling pathway. It follows that any agent that disrupts or prevents this binding will also inhibit IL-2 dependent signalling. Thus, we have designed an assay to identify compounds that inhibit interactions between components of the IL-2 receptor complex as a method for identifying candidate agents for modulating the immune system.

Direct physical interactions of IL-2Rβ with JAK-1 and $\gamma_c$ with JAK-3 were demonstrated during the development of the present invention. IL-2 increased JAK-3 association with the IL-2 receptor, with an apparent increase of $\gamma_c$-JAK-3 association and de novo induction of IL-2Rβ-JAK-3 interaction. Truncation of $\gamma_c$ resulted in its failure to associate with JAK-3. Moreover, a patient having a mild form of X-linked combined immunodefficiency (XCID) that was characterized by diminished IL-2 induced proliferation had a $\gamma_c$ point mutation (Leu 271 changed to Gln) that decreased $\gamma_c$ association with JAK-3. Thus, $\gamma_c$ mutations, in at least some XSCID and XCID patients, can inhibit the ability of $\gamma_c$ to associate with JAK-3. The severity of this immunodeficiency owes to the fact that $\gamma_c$ is a component of multiple cytokine receptors.

Indeed, the sharing of the $\gamma_c$ subunit of the IL-2 receptor by other cytokine receptors, including receptors for IL-4, IL-7, IL-9 and IL-15, has led us to believe that any compound which inhibits the cytokine induced binding of JAK-3 to the $\gamma_c$ chain would also inhibit signalling through the receptors for any of these cytokines. Thus, we believe that an assay for compounds that inhibit cytokine induced binding of JAK-3 to the $\gamma_c$ chain is useful in the discovery of drugs that could be used to treat autoimmune diseases that are attributable to the activities of IL-2, IL-4, IL-7, IL-9 and IL-15.

Although other materials and methods similar or equivalent to those described herein can be used in the practice or testing of the present invention, the preferred methods and materials are now described. General references for methods that can be used to perform the various PCR and cloning procedures and nucleic acid and protein blotting procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987). The disclosures contained in these publications are hereby incorporated by reference. A description of the experiments and results that led to the creation of the present invention follows.

We employed the PCR approach described by Harpur et al., in *Oncogene* 7:1347 (1992) and by Siliciano et al., in *Proc. Natl. Acad. Sci. USA* 89:11194 (1992) to amplify novel PTK encoding sequences expressed in NK cells. The disclosures of these Harpur et al. and Siliciano et al. references are incorporated by reference. Briefly, we first prepared cDNA from NK cell mRNA using reverse transcriptase. We then performed PCR using degenerate oligonucleotide primers corresponding to conserved motifs in the catalytic domains of PTK. The forward primers were designed to correspond to residues in subdomain VI and to exclude src-family PTK. The reverse primer corresponded to the reverse complement of the DVWSFG (SEQ ID NO:1) motif (subdomain IX) conserved in a large number of PTK.

Example 1 describes the methods used to isolate an amplified polynucleotide that corresponded to the JAK-3 tyrosine kinase.

EXAMPLE 1

PCR Amplification of a Novel NK Cell Derived Protein Tyrosine Kinase

First strand cDNA was prepared from total RNA that had been isolated from NK cell RNA according to standard methods. The cDNA prepared in this fashion served as the template in a subsequent PCR reaction.

The forward primer used in this PCR reaction was 5'-CCA GCG GCC GCG T(G/A/T/C)CA (C/T)CG (G/A/T/C)GA (C/T)C T(G/A/T/C)GC-3' (SEQ ID NO:2) and the reverse primer was 5'-CCA GCG GCC GCC C(G/A)A A(G/A/T/C/) (G/C) (A/T)CC A(G/A/T/C)A C(G/A)T C-3' (SEQ ID NO:3). The resulting products were digested with NotI, subcloned and sequenced. The PCR fragment corresponding to one novel kinase was isolated, labeled and used to screen several cDNA libraries. Among the libraries screened were oligo (dT) primed cDNA libraries derived from PHA stimulated peripheral blood T-cells and the HUT-78 T-cell line (Clonetech, Palo Alto, Calif.) in the λgtll cloning vector, a λ ZAP YT library and a λ ZAP library from PHA activated T-cells. Purified phage DNA was digested and subcloned into pBLUESCRIPT (Stratagene, La Jolla, Calif.) for nucleic acid sequencing. Sequence data were manipulated and analyzed using the programs of the Genetics Computer Group of the University of Wisconsin and the BLAST program of NCBI.

For Northern analysis, total RNA from various human tissues was either purchased from Clonetech (Palo Alto, Calif.) or prepared from NK cells and T-cells. Northern blotting was carried out according to standard procedures. Blots were probed with radiolabeled nucleic acid probes corresponding to the PCR amplified fragment described above.

Results indicated that one of the candidate clones isolated by this method was preferentially expressed in NK and activated T-cells as an approximately 4.3 kb mRNA.

Thus, the DNA fragment amplified using kinase-specific primers exhibited a tissue-specific pattern of mRNA expression. We therefore proceeded to isolate a cDNA clone that contained the entire reading frame for the protein that was partly encoded by the amplified fragment. We have termed this protein "JAK-3."

Example 2 describes the method used to determine the DNA sequence of the polynucleotide that encoded the putative tissue-restricted kinase obtained in Example 1.

EXAMPLE 2

Isolation and Analysis of a Polynucleotide Encoding JAK-3

The PCR generated fragment from Example 1 was used as a probe to screen phage cDNA libraries prepared from the NK-like cell line, YT, PHA-activated T-cells and HUT-78 cells. Approximately 5×10$^5$ plaques from each library were screened to obtain multiple overlapping clones that generated a polynucleotide sequence corresponding to a single long open reading frame. SEQ ID NO:9 provides the predicted amino acid sequence encoded by the NK cell derived JAK-3 cDNA. We note that a published report by Kawamura et al. (*Proc. Natl. Acad. Sci. USA* 91:6374 (1994)) refers to the JAK-3 protein disclosed herein as "L-JAK." The polynucleotide sequence encoding the JAK-3 protein has been filed in GenBank under accession number U09607 and is provided herein as SEQ ID NO:8.

The open-reading frame of this polynucleotide sequence encompasses 3372 nucleotides and is predicted to encode a polypeptide having 1124 residues. The molecular weight of the predicted polypeptide is 125,014 Da. This value is roughly equivalent to, but slightly smaller than, other JAKs. As described below, this predicted molecular weight is consistent with the $M_r$ of the polypeptide identified by Western blotting using the antiserum prepared against JAK-3.

The predicted protein encoded by the JAK-3 polynucleotide exhibited structural features characteristic of a PTK, as would readily be appreciated by one having ordinary skill in the art. Like other PTK, a catalytic domain is present in the C-terminal portion of the molecule (subdomains I–XI). This domain begins with a typical ATP-binding motif at residues 829–834 (subdomain 1) in which the canonical GXGXXG (SEQ ID NO:4) motif is evident and is followed by a critical lysine residue in subdomain II (residue 855). Just C-terminal to subdomain VII is a pair of tyrosine residues following an acidic residue that could represent the autophosphorylation site. In subdomain VIII, phenylalanine and tyrosine residues surround the invariant tryptophan residue. We note that the locations of the subdomains cited herein are identified by Kawamura et al. in *Proc. Natl. Acad. Sci. USA* 91:6374 (1994), the disclosure of which is hereby incorporated by reference. This atypical motif contrasts with the motifs seen in src and abl related proteins, and growth factor receptors. Notably though, this motif (FWYAPE) (SEQ ID NO:5) is present in the Janus family kinases. The Janus family of PTK comprises PTK that have tandem nonidentical catalytic domains and a large extracatalytic segment. These structural features of the Janus family of PTK have been considered by Wilks et al., in *Mol. Cell. Biol.* 11:2057 (1991), Harpur et al., in *Oncogene* 7:1347 (1992), and Firmbach-Kraft et al., in *Oncogene* 5:1329 (1990). The entire catalytic domain, termed the JAK homology (JH) 1 domain, comprises 273 amino acids (residues 822 to 1095) and is followed by a unique C-terminus.

In addition to a kinase catalytic domain, the predicted JAK-3 protein has a region N-terminal to the PTK catalytic domain that also has elements typical of a protein kinase catalytic domain. This tandem kinase-like (JH-2) domain is a characteristic feature of the JAKs, and has been described by Harpur et al., in *Oncogene* 7:1347 (1992), Firmbach-Kraft et al., in *Oncogene* 5:1329 (1990), Velazquez et al., in *Cell* 70:313 (1992), and Argetsinger et al., *Cell* 74:237 (1993). Like other Janus family kinases, this domain in the NK derived JAK-3 protein lacks some standard features of a PTK catalytic domain. In particular, the JAK-3 protein appears to lack an autophosphorylation site in subdomain VII.

The known JAK family PTK have large extracatalytic segments (JH 3–7 domains) located N-terminal to the kinase (JH1) and kinase-like (JH2) domains. While motifs corresponding to SH2 or SH3 domains are lacking, there is a motif that Harpur et al., (*Oncogene* 7:1347 (1992)) suggested to have SH2-like character. This region is conserved in three of the four family members, including the JAK-3 protein. Immediately N-terminal to this motif is a highly conserved motif that is a possible tyrosine phosphorylation site (VDGYFRL) (SEQ ID NO:6). Other areas of striking homology between the novel JAK-3 protein and other JAKs are also evident in the remaining domains (JH 5–7).

The findings presented above indicated the NK-derived isolate had nearly all of the characteristics of a JAK family PTK. Protein homology analysis indicated the overall identity of the NK PTK to the most closely related Janus family member, JAK-2, was approximately 68%. The fact that a hydrophilicity plot showed no evidence for a hydrophobic domain suggested that the JAK-3 polynucleotide sequence encoded a non-receptor type PTK.

Other members of the Janus family of PTK (JAK-1, JAK-2, and Tyk2) have been shown to be present in a variety of tissues. These findings have been described by Wilks et al., in *Mol. Cell. Biol.* 11:2057 (1991), Harpur et al., in *Oncogene* 7:1347 (1992), and Firmbach-Kraft et al., in *Oncogene* 5:1329 (1990). Given this precedent, we proceeded to determine if JAK-3 was also broadly expressed across different tissues and cell types. As described below, we unexpectedly discovered that JAK-3 expression is tissue-restricted.

Example 3 describes the methods used to determine the expression profile for the JAK-3 mRNA.

EXAMPLE 3

Expression of the JAK-3 mRNA

Total RNA (20 µg) from various human tissues (purchased from Clonetech), NK cells and T-cells was electrophoresed in formaldehyde/agarose gels, transferred to membranes and probed with a radiolabeled cDNA corresponding to the JH1 and JH2 domains of JAK-3. T-cells were activated with PHA for 24 hours prior to RNA isolation. NK cells were activated with IL-2 (1,000 units/ml) for 24 hours prior to RNA isolation. Uniform RNA loading in the different lanes of the Northern blot was confirmed by ethidium bromide staining and by hybridization with a probe that detected ribosomal RNA.

Unexpectedly, and in contrast to other Janus family members, JAK-3 exhibited a restricted pattern of mRNA expression across different tissues. In the absence of stimulation, the mRNA was only detected in NK cells. Notably, activation of NK cells did not alter the level of JAK-3 mRNA expression. The JAK-3 mRNA was also detected at high levels in activated NK cells and activated T-cells. No JAK-3 mRNA was detected in liver, testis, kidney, small intestine, brain or lung tissues. Hybridization of the same Northern Filter with a JAK-1 cDNA probe gave evidence for mRNA expression in all tissues except for small intestine. Interestingly, while the JAK-3 mRNA was expressed at very low levels in resting T-cells, the mRNA was induced upon T-cell activation.

Various cultured cell lines were also tested for expression of the JAK-3 mRNA. As expected, our results indicated the JAK-3 mRNA was constitutively expressed in the NK-like YT cell line. As predicted by studies with peripheral blood T-cells, the JAK-3 mRNA was not constitutively expressed in the Jurkat T-cell line but was induced upon activation. Interestingly, we found that JAK-3 mRNA was constitutively expressed in the HUT-78 transformed T-cell line. No expression of this gene was detected in a variety of other cell lines, including the erythroleukemia cell line, K562.

We next identified a unique portion of the C-terminal region of the JAK-3 protein and generated a corresponding synthetic peptide for use as an immunogen. The conclusion regarding protein sequence uniqueness was based on the results from a computer-assisted comparison between the JAK-3 amino acid sequence and all sequences available through the Program Manual for the Wisconson Package, Version 8, September 1994, Genetics Computer Group, (575 Science Dr. Madison, Wis. 53711). This search protocol included searches of the GenBank, GenPept, SwissProt, Brookhaven and EMBL databases. The synthetic peptide used in our procedures corresponded to amino acids 1104–1124 of the JAK-3 protein.

Example 4 describes the immunological methods used to analyze the JAK-3 protein.

EXAMPLE 4

Identification of the JAK-3 Protein by Metabolic Labeling and Immunoprecipitation A peptide corresponding to the predicted C-terminus of the JAK-3 protein (amino acids 1104–1124) was synthesized (Multiple Peptide Systems, San Diego, Calif.), coupled to keyhole limpet hemocyanin (KLH) with MBS (Pierce, Rockford, Ill.) and used to immunize rabbits. HUT-78 cells ($10^7$ cells per point) were labeled with $^{35}$S methionine (0.5 mCi/ml) for 2 hours, washed with phosphate buffered saline and lysed in buffer containing 1% TRITON™ X-100 (lysis buffer). Postnuclear supernatants were immunoprecipitated with 10 µl of antiserum prebound to protein A sepharose washed in buffer containing 0.1% TRITON™ X-100 (wash buffer), eluted and electrophoresed in 8% polyacrylamide gels that were subsequently fixed, rinsed in FLUOROHANCE™ (Research Products Inc., Mount Prospect, Ill.) and dried for autoradiography.

For immunoblot analysis, cells were solubilized in lysis buffer and postnuclear supernatants (approximately 100 µg of protein) were electrophoresed, transferred to nitrocellulose and immunoblotted. Filters were blocked, incubated with antiserum (1:1000), washed and incubated with peroxidase conjugated goat antirabbit IgG, all according to standard methods well known in the art. Antibody binding was detected by enhanced chemiluminescence (ECL) (Amersham Corp.).

In good agreement with the molecular weight predicted by the deduced JAK-3 primary structure, analysis of metabolically labeled HUT-78 cells showed specific immunoprecipitation of a polypeptide with a $M_r$ of approximately 125 kDa. Immunoblot analysis of these cells also showed reactivity of the antibody with a protein of approximately the same mobility in HUT-78. In contrast Jurkat T-cells expressed minimal levels of this protein. In additional experiments, the expression of the JAK-3 encoded polypeptide was found to parallel the expression seen by analysis of mRNA. Expression of the protein was detected in NK cells, activated T-cells and in some transformed leukocyte cell lines. Immunoblotting with preimmune serum or antiserum competed with cognate peptide versus irrelevant peptide, thus confirming the specificity of this reactivity.

The results obtained in Example 4 confirmed that antibodies raised against a JAK-3 specific synthetic peptide could be used to immunoprecipitate the JAK-3 protein from cellular lysates. However, these results provided no insight into the function of the JAK-3 protein. Thus, to ascertain whether the JAK-3 protein had enzymatic activity, in vitro kinase assays were performed.

Example 5 describes the in vitro assay used to demonstrate that immunoprecipitated JAK-3 protein had kinase activity.

EXAMPLE 5

JAK-3 In Vitro Kinase Activity

Kinase assays were performed as described by Muller et al., in *Nature* 366:129 (1993), and by Watling et al., in *Nature* 366:166 (1993). According to these procedures, cells were solubilized in lysis buffer supplemented with 1 mM $Na_3VO_4$ and 1 mM EDTA. An antipeptide antiserum was then used to carry out an immunoprecipitation reaction. Washed immunoprecipitates were incubated in 50 μl of buffer containing 20 mM Tris, 5 mM $MgCl_2$, 5 mM MnCl, 1 μM ATP, and 200 μCi/ml $^{32}$P-ATP (Amersham Corp.). The reaction was carried out for 15 minutes at 25° C. and was terminated by the addition of ice cold wash buffer. After washing the beads again, the reaction products were eluted, electrophoresed and autoradiographed.

A phosphorylated polypeptide having the expected 125 kDa molecular weight was evident in immunoprecipitates from NK cells but not in immunoprecipitates from resting T-cells or untreated control cells. The phosphorylated residues were resistant to KOH, consistent with tyrosyl phosphorylation. We concluded that this tyrosyl phosphorylation likely represented autophosphorylation of JAK-3.

Thus, our results indicated the novel JAK-3 protein had both structural and functional characteristics of a protein tyrosine kinase related to the Janus family of PTK. In an effort to discern the role of JAK-3 in cellular physiology, we made a more extensive investigation into the range of cell types that expressed the JAK-3 protein.

Example 6 describes the method used to determine the range of cell types that express JAK-3 protein.

EXAMPLE 6

Expression of the JAK-3 Protein in Activated T-Cells and NK Cells

Whole cell lysates from human peripheral blood T-cells (unstimulated or stimulated for 48 hours with PHA), the transformed T-cell lines Hut78 and YT, peripheral blood NK cells, the NK 3.3 cell line, human peripheral blood monocytes, the myelomonocytic cell lines U937 and THP-1, and the tumor cell line OVCAR-3, HT-29 and IM-9 were run on SDS-PAGE and were probed with antisera to JAK-3. Human peripheral blood T lymphocytes, NK cells and monocytes (>97% pure) were obtained by leukophoresis and column purification according to standard procedures. T lymphocytes were either untreated or treated with PHA (10 μg/ml) and incubated for 0–48 hours. Cells were grown in RPMI 1640 supplemented with calf serum. Cells were lysed in buffer containing TRITON™ 100 and clarified lysates (50 μg) were run on SDS PAGE, transferred to IMMOBILON™ GELS and probed with anti-JAK-3 antisera and HRP-conjugated antirabbit immunoglobulin. Immunoblots were developed with enhanced chemiluminescence (Amersham) using standard procedures. The anti-JAK-3 antiserum used in these procedures was raised against a synthetic peptide corresponding to the C-terminal region of the JAK-3 protein (amino acids 1104–1124), and has been described by Kawamura et al., in *Proc. Natl. Acad. Sci. USA* 91:6374 (1994).

The results from these procedures indicated that JAK-3 was expressed only in a limited spectrum of tissue types. It was strongly expressed in NK cells, the NK cell line NK 3.3, YT cells and in the transformed T-cell line Hut78 as judged by the presence of a 125 kDa band on the Western blot. The JAK-3 protein was not detected in other cell types that were examined. In contrast to the pattern of JAK-3 protein expression, other JAK family kinases are known to be expressed in both lymphoid and nonlymphoid cells. While JAK-3 was expressed at low levels in resting peripheral blood T-cells, these levels of expression were greatly increased following activation by either PHA or anti-CD3.

The induction of the IL-2 gene and IL-2 receptor α chain are among the critical events that occur during T-cell activation. These factors have been considered by Taniguchi in *Ann. Rev. Immunol.* 4:69 (1988), and by Leonard et al., in *Proc. Natl. Acad. Sci. USA* 80:6957 (1983). As the induction of these genes paralleled the induction of JAK-3, we investigated the possibility that JAK-3 was somehow coupled to the IL-2 receptor. Indeed, in *Cell* 74:587 (1993), Stahl et al. disclosed that occupancy of certain other cytokine receptors induced tyrosine phosphorylation of other JAKs.

Example 7 describes the methods used to demonstrate that the JAK-3 protein is inducibly phosphorylated by IL-2 stimulation of T and NK cell lines, and peripheral blood NK cells.

EXAMPLE 7

Tyrosine Phosphorylation of JAK-3 in Response to IL-2

Cells were either unstimulated or stimulated with IL-2 (1000 U/ml) for 5 minutes, then lysed, immunoprecipitated with anti-JAK-3 antisera and immunoblotted and probed with a monoclonal antiphosphotyrosine antibody (4G10 UBI). In this procedure, cells were washed twice with RPMI that had been acidified at pH 6.5 before incubation for 3 hours with 0.5% human serum. The cells were again washed twice before stimulation with IL-2. The cells were lysed in buffer containing TRITON™ X-100 prior to the immunoprecipitation procedure. Detection of the antiphosphotyrosine antibody probe bound to the 125 kDa JAK-3 protein band was by autoradiography.

Using this procedure, we found that IL-2 induced tyrosine phosphorylation of JAK-3 in YT (T-cell line) and NK 3.3 (NK cell line) cells as well as in peripheral blood NK cells. We observed little basal tyrosine phosphorylation of JAK-3 in any of the cell samples that were tested. However, after 5 minutes of IL-2 stimulation, intense phosphorylation of a protein band having a molecular weight of 125 kDa was evident on the autoradiograph. This band represented the JAK-3 protein. A constitutively expressed phosphoprotein band that migrated at a discrete position in the gel between the 69 and 96 kDa molecular weight markers was observed in YT and NK3.3 cell lines, and in peripheral blood NK cells. A second constitutive phosphoprotein band was observed in the NK3.3 lanes on the autoradiograph. In aggregate, these results indicated that JAK-3 is a protein that is inducibly phosphorylated by stimulation of T-cells and NK cells with IL-2.

IL-2 induced tyrosine phosphorylation in the Hut78 T-cell line was also examined in a time course experiment. Lysates from Hut78 cells either untreated or treated with IL-2 for 5, 10 or 30 minutes were immunoprecipitated with anti-JAK-3 and blotted with antiphosphotyrosine antibody and with anti-JAK-3. Our results indicated that Hut78 cells showed induction of JAK-3 tyrosine phosphorylation after treatment with IL-2 that was maximal at 10 minutes. Prior absorbance of the JAK-3 antiserum with cognate peptide eliminated the tyrosine phosphorylated protein at 125 kDa and thereby confirmed the specificity of the tyrosine phosphorylated band as JAK-3. JAK-3 was also found to be phosphorylated in response to IL-2 in human peripheral blood T-cells that had been pre-activated with PHA for 24 hours. Thus in human T and NK cells, T-cell and NK cell lines, IL-2 induced the rapid tyrosyl phosphorylation of JAK-3 protein.

Both Farrar, et al. (*J. Biol. Chem.* 264:12,562 (1989)) and Kirken, et al., (*J. Biol Chem.* 268:22,765 (1993)) have disclosed that IL-2 stimulation induced tyrosyl phosphorylation of a variety of substrates in human peripheral blood T-cells and T-cell lines. In the following Example, we demonstrated that the most prominent phosphotyrosyl protein evident following IL-2 stimulation of the YT cell line was a polypeptide of 125 kDa that comigrated with JAK-3. To confirm the identity of this 125 kDa substrate as JAK-3, an experiment was conducted in which lysates from IL-2 treated cells were first depleted of JAK-3 prior to immunoprecipitation with antiphosphotyrosine antibodies. In addition, we examined whether the other JAK family members could be activated by IL-2.

Example 8 describes the methods used to demonstrate that JAK-1 and JAK-3 are tyrosine phosphorylated in T-cells upon IL-2 stimulation.

EXAMPLE 8

IL-2 Induced Tyrosyl Phosphorylation of JAK Family Kinases

Serum-starved YT cells were treated with IL-2 (1000 U/ml) for 0 or 15 minutes. Cells were lysed in buffer containing TRITON™ X-100 and phosphatase inhibitors and then immunoprecipitated with an antiphosphotyrosine antibody bound to protein G sepharose. Lysates were precleared with either rabbit polyclonal antisera, anti-JAK-3 or anti-JAK-1 before immunoprecipitation and immunoblotting with anti-phosphotyrosine. As a positive control to identify the position of JAK-3 on the Western blot, a sample of the lysate from IL-2 induced cells was immunoprecipitated with anti-JAK-3 and blotted with antiphosphotyrosine. All immunoprecipitates were subjected to SDS-PAGE and transferred to IMMOBILON™ GELS.

Depletion of YT cell lysates with anti-JAK-3 antiserum specifically removed the 125 kDa tyrosine phosphorylated protein, thus indicating that JAK-3 was one of the most prominent phosphoproteins detected in response to IL-2 in these cells. Conversely, depletion of lysates with anti-JAK-1 did not remove this phosphoprotein. This result clearly established that JAK-3 is a prominent tyrosyl phosphoprotein in IL-2 induced T-cells.

In addition, we examined whether other JAK family members could be activated by IL-2. An experiment similar to that described above was performed in which antiphosphotyrosine immunoblots were purposely overexposed to reveal other substrates. In particular, YT cells were treated with IL-2 (1000 U/ml) for 0, 5 or 15 minutes, lysed, immunoprecipitated with anti-phosphotyrosine and subsequently immunoblotted with anti-phosphotyrosine, and anti-JAK-3 or anti-JAK-1. We observed a tyrosyl phosphoprotein induced in response to IL-2 that was larger in size than JAK-3. Immunoprecipitation with anti-JAK-1 antiserum and immunoblotting with antiphosphotyrosine confirmed that this protein was JAK-1. Although both Tyk2 and JAK-2 could be detected in YT cells, no tyrosyl phosphorylation of either protein was observed in response to IL-2 stimulation.

Thus, the results obtained in Example 8 indicated that IL-2 stimulation of T-cells led to tyrosine phosphorylation of JAK-3 and, to a somewhat lesser extent, of JAK-1.

Example 9 describes the methods used to demonstrate that IL-2 stimulates JAK-3 in vitro kinase activity.

EXAMPLE 9

IL-2 Stimulates JAK-3 in vitro Kinase Activity

Cells were treated with IL-2 (1000 U/ml) for 0, 10 or 20 minutes. In vitro kinase activity was measured in anti-JAK-3 immunoprecipitates. For measurement of in vitro kinase activity, immunoprecipitates were washed in 50 mM NaCl, 5 mM $MgCl_2$, 5 mM $MnCl_2$, 0.1 mM $Na_3VO_4$, 10 mM HEPES (pH 7.4) and incubated in the same buffer containing 0.25 µCi/ml [$^{32}$P-γ]ATP for 15 minutes at room temperature. After three washes, proteins were eluted in sample buffer and analyzed by SDS-PAGE. Gels were either dried or transferred to IMMOBILON™ gels before exposure. Autophosphorylation signals were detected by autoradiography of the dried gels. JAK-3 in vitro kinase activity in response to IL-2 stimulation (15 minutes) was measured in immunoprecipitates from peripheral blood NK cells and Hut78 cells. JAK-3 immunoprecipitated from YT cells activated in response to IL-2 displayed elevated kinase activity that peaked at approximately 10 minutes. Similar results were obtained using human peripheral blood NK cells and Hut78 cells. This kinase activity was not precipitated by preimmune serum or in the presence of competing JAK-3 peptide. These results confirmed that the observed kinase activity was specific for the JAK-3 protein. The vast majority of the phosphorylation observed was attributable to phosphorylation of tyrosine residues as demonstrated by resistance to KOH treatment and by phosphoamino acid analysis.

We next examined JAK-3 phosphorylation in YT cells following stimulation by a number of these cytokines. Other members of the JAK family have been shown to be activated by several lymphokines including the interferons (IFNs), erythropoietin (EPO), growth hormone (GH) and IL-3 (Witthuhn et al., *Cell* 74:227 (1993); Argetsinger et al., *Cell* 74:237 (1993); Silvennoinen et al., *Proc. Natl. Acad. Sci. USA* 90:8429 (1993)). JAK-3 was tyrosine phosphorylated in response to IL-2, but not in response to GH, IFN-α or IFN-γ in the YT cells. We did detect tyrosine phosphorylation of JAK-2 in response to IFN-γ in these cells, thus confirming the activity of this cytokine. Stimulation of YT cells with IL-3, GM-CSF or EPO also failed to induce JAK-3 phosphorylation. IL-4 has recently been shown to utilize the common γ chain of the IL-2 receptor (γc), suggesting that common signaling pathways also may be utilized by these cytokines (see Russell et al., *Science* 262:1880 (1993), and Kondo et al., *Science* 262:1874 (1993)). This knowledge prompted us to examine whether JAK-3 was also activated in response to IL-4.

Example 10 describes the methods used to test whether other cytokines, in addition to IL-2, induced JAK-3 tyrosine phosphorylation.

EXAMPLE 10

Phosphorylation of JAK-3 in Response to Cytokines Other than IL-2

YT cells were serum-starved for 3 hours and acid washed twice before stimulation and immunoprecipitation. NK 3.3 cells were grown for 2 days in 10% lymphocult (Biotest) and 15% fetal bovine serum before being washed and incubated in 2% serum. Commercial polyclonal anti-JAK-1 and JAK-2 antisera were obtained from UBI and Tyk2 polyclonal antiserum from Santa Cruz Biotechnology.

Lysates of YT cells that were unstimulated or stimulated with IL-2 (1000 U/ml), GH (50 ng/ml), IFN-α (1000 U/ml) or IFN-γ (500 U/ml) for 15 minutes were immunoprecipitated with anti-JAK-3 and blotted with antiphosphotyrosine. Results from this Western blotting experiment proved that JAK-3 was tyrosine phosphorylated in response to IL-2, but not in response to GH, IFN-α or IFN-γ. In addition, JAK-3 was not phosphorylated in response to IL-3, granulocyte macrophage colony stimulating factor (GM-CSF) or erythropoietin, all of which have been shown to activate JAK-2.

In related procedures, NK 3.3 cells that were incubated overnight in 2% serum were stimulated with IL-2 (1000 U/ml), IL-4 (100 U/ml) or IFN-γ (500 U/ml) for 5 or 15 minutes. Cellular lysates were immunoprecipitated with anti-JAK-3 and blotted with antiphosphotyrosine. Results from these procedures indicated that JAK-3 was tyrosine phosphorylated in response to both IL-4 and IL-2 in NK 3.3 cells. These results confirmed that the JAK-3 kinase is involved in signaling pathways other than IL-2.

Given these findings, we proceeded to investigate the detailed mechanism by which the JAK proteins were involved in IL-2 mediated signal transduction. As described in the following Examples, we discovered that two of the IL-2 receptor subunits interacted with the JAKs. In particular, we discovered that the JAK-1 and JAK-3 proteins physically interacted with the IL-2Rβ and $\gamma_c$ IL-2 receptor subunits. Further, the $\gamma_c$-JAK-3 binding was found to be induced by IL-2 stimulation. Our procedures began with a demonstration that both the JAK-1 and JAK-3 proteins are phosphorylated by IL-2 stimulation.

Example 11 describes methods that can be used to detect phosphorylation of the JAK-1 and JAK-3 proteins.

EXAMPLE 11

IL-2 Stimulation Induces Phosphorylation of JAK-1 and JAK-3

Peripheral blood lymphocytes (PBL) were induced for 15 minutes with IL-2 (1000 U/ml), IL-4 (100 U/ml), IL-7 (100 ng/ml), or IL-9 (100 ng/ml) after phytohemagglutinin (PHA) stimulation. The PBL were activated for 72 hours with PHA, then washed twice at pH 6.5, incubated for 3 hours in medium containing 0.5% human serum and resuspended in medium containing 10% fetal calf serum for one hour. Cells were then lysed and immunoprecipitated with polyclonal antibodies to JAK-1 (UBI) or JAK-3. The anti-JAK-3 antibody used in these procedures has been described by Johnston et al., in *Nature* 370:151 (1994). Phosphotyrosine-containing proteins were detected by immunoblotting with 4G10 (UBI). NK3.3 cells were stimulated with IFN-α (1000 U/ml) or IL-2 (1000 U/ml), immunoprecipitated with polyclonal antibodies to Tyk2 (UBI) or JAK-2 (UBI) and immunoblotted with 4G10 mAb to phosphotyrosine (UBI). In one procedure, the lysate was precleared with polyclonal antibody to JAK-3.

Although immunoprecipitation with antibodies to JAK-2 yielded a tyrosine phosphorylated band in response to IL-2, this band migrated faster than the JAK-2 band induced by interferon-γ and was human JAK-3, immunoprecipitated through cross-reactivity with the JAK-2 antiserum. This was demonstrated by elimination of this band by preclearing the lysate with a JAK-3 specific antiserum. In addition to IL-2, we tested three other known $\gamma_c$ users, IL-4, IL-7 and IL-9, for their abilities to induce the tyrosine phosphorylation of JAK-1 and JAK-3. Each of these cytokines induced tyrosine phosphorylation of both JAK-1 and JAK-3 in Western blotting procedures and activated both JAK-1 and JAK-3 as evaluated by in vitro kinase assays. Thus, cytokines that signal using mechanisms that involve the common $\gamma_c$ subunit induce phosphorylation of JAK-1 and JAK-3.

Given the essential roles of both IL-2Rβ and $\gamma_c$ in IL-2 signal transduction, we investigated the ability of each of these chains to physically associate with JAK-1 and/or JAK-3, the two Janus kinases that were activated and tyrosine phosphorylated in response to IL-2. YT cellular lysates were immunoprecipitated with Mikβ1 (anti-IL-2Rβ) monoclonal antibody (mAb) or R878 (anti-$\gamma_c$) antiserum, followed by Western blotting with JAK-3 and reblotting with JAK-1.

Example 12 describes the methods used to demonstrate that JAK-1 binds the IL-2Rβ subunit, and that JAK-3 binds the $\gamma_c$ subunit of the IL-2 receptor.

EXAMPLE 12

Physical Association of JAK-1 and JAK-3 with Components of the IL-2 Receptor

YT cells were either stimulated or not stimulated with IL-2 and then lysed with 10 mM Tris (pH 7.5) containing 2 mM EDTA, 0.15 M NaCl, 0.875% Brij 96, 0.125% NONIDET P40™, 0.4 mM sodium vanadate, 1 mM 4-(2-aminoethyl)-benzenesulfonyl fluoride hydrochloride (ICN), 2.5 mM leupeptin, 2.5 mM aprotinin. Immunoprecipitations were performed using Mikβ1 anti-IL-2Rβ mAb, R878 antiserum to $\gamma_c$, or RPC5 (control mAb). The gel was Western blotted sequentially with antisera to JAK-3 and then JAK-1 using ECL. The object of this coprecipitation procedure was to test whether precipitation of one subunit of the IL-2 receptor would also precipitate one of the JAK proteins.

Our results indicated that JAK-1 constitutively associated with IL-2Rβ, and that the quantitative extent of association did not increase following IL-2 stimulation. JAK-1 did not constitutively associate with $\gamma_c$, but after IL-2 stimulation and the induction of association of IL-2Rβ with $\gamma_c$, some JAK-1 coprecipitated with $\gamma_c$. Although JAK-1 weakly associated with $\gamma_c$ in the absence of IL-2, this association increased following IL-2 stimulation. Moreover, after IL-2 stimulation, JAK-3 was readily coprecipitated with anti-IL-2Rβ mAb Mikβ1 or TU11. This was expected for TU11, which binds to an IL-2Rβ epitope distinct from the IL-2 binding site and coprecipitates $\gamma_c$ in the presence but not absence of IL-2, but was unexpected for Mikβ1, which competes for IL-2 binding and cannot coprecipitate $\gamma_c$ in the presence or absence of IL-2.

These data indicated that IL-2Rβ primarily associated with JAK-1 and that $\gamma_c$ associated with JAK-3. However, interactions between IL-2Rβ and JAK-3 also occurred. Though the basis for the IL-2 induced association of IL-2Rβ with JAK-3 is unknown, IL-2 induced heterodimerization of IL-2Rβ and $\gamma_c$ may juxtapose JAK-3 to IL-2Rβ, thus facilitating their interaction. Significantly, the association of JAK-3 with $\gamma_c$ was induced by IL-2.

To further evaluate the association of IL-2Rβ and $\gamma_c$ with JAK-1, we transiently transfected COS-7 cells with cDNAs encoding JAK-1 and either IL-2Rβ or $\gamma_c$.

Example 13 describes a cotransfection procedure that confirmed the physical interaction between JAK-1 and IL-2Rβ. The results of this procedure did not provide evidence for an interaction between JAK-1 and the $\gamma_c$ receptor subunit.

EXAMPLE 13

Recombinant JAK-1 Associates with Recombinant IL-2Rβ in Transfected Cells

Cotransfection of COS-7 cells with JAK-1 and either IL-2Rβ or $\gamma_c$ expression constructs was followed by immunoprecipitation and Western blotting with Erd A antiserum to IL-2Rβ, R878 antiserum to $\gamma_c$ or antiserum to JAK-1. The IL-2Rβ expression construct used in this procedure consisted of the IL-2Rβ1 cDNA insert described by Gnarra et al., in *Proc. Natl. Acad. Sci. USA* 87:3440 (1990), under transcriptional control of the SRα promoter that has been described by Takebe et al., in *Mol. Cell. Biol.* 8:466 (1988). The $\gamma_c$ expression construct used in this procedure included a $\gamma_c$ cDNA insert derived from a clone that was isolated from a cDNA library prepared from YT cell mRNA. The 5' end of the $\gamma_c$ cDNA insert corresponded to position −43 as presented in FIG. 2 by Noguchi et al., in *J. Biol. Chem.* 268:13601 (1993), and extended to the 3' end of the full length $\gamma_c$ sequence that has been presented by Takeshita et al., in *Science* 257:379 (1992). The JAK-1 expression construct used in this procedure had the JAK-1 cDNA under transcriptional control of the CMV promoter. When JAK-1 and IL-2Rβ expression constructs were cotransfected, antibodies to either protein coprecipitated the other as evaluated by Western blotting. As expected, the RPC5 control mAb failed to immunoprecipitate material that could be identified by either the anti-JAK-1 or the anti-IL-2Rβ antiserum on the Western blot. This negative result confirmed the specificity of the blotting procedure. The Gnarra et al., Takebe et al., Noguchi et al., and Takeshita et al. references referred to in this example are all incorporated herein by reference.

Our results also indicated that $\gamma_c$ and JAK-1 did not associate with each other. This latter finding was evidenced by the inability of anti-JAK-1 to immunoprecipitate material that could be stained on Western blots probed with anti-$\gamma_c$ antibodies, and by the inability of anti-$\gamma_c$ to immunoprecipitate material that could be stained on Western blots probed with anti-JAK-1. On the other hand, anti-JAK-1 immunoprecipitated material that was stained by anti-JAK-1, and anti-$\gamma_c$ antibodies immunoprecipitated material that was stained by anti-$\gamma_c$ antibodies. This latter observation confirmed the integrity of the reagents used in these procedures. As expected, the RPC5 control mAb failed to immunoprecipitate material that was stained by either anti-JAK1 or anti-IL-2Rβ antiserum on the Western blot. Although the positive control procedures confirmed our ability to detect all relevant protein species, we did not obtain any evidence for an association between JAK-1 and the $\gamma_c$ receptor chain. However, these findings did confirm a physical association between JAK-1 and IL-2Rβ.

We conducted an experiment to determine the relative importance of the cytoplasmic domain of the IL-2Rβ receptor chain, and to test the importance of the extracellular domain with respect to facilitating the interaction between JAK-1 and the IL-2Rβ chain. COS-7 cells were cotransfected with JAK-1 and either IL-2Rα, chimeric α/α/β or chimeric α/γ/γ expression constructs according to standard protocols. The structures of the chimeric constructs encoding these novel receptor chains has been described by Nakamura et al., in *Nature* 369:330 (1994), the disclosure of which is hereby incorporated by reference. The RPC5 control mAb and anti-Tac mAb to IL-2Rα were separately used for immunoprecipitations that were followed by Western blotting with antiserum to JAK-1. Neither anti-Tac nor RPC5 antibodies immunoprecipitated material from lysates of JAK-1 and IL-2Rα cotransfectants that was also stained by anti-JAK-1. Thus, there was no evidence that JAK-1 interacted with any portion of the IL-2Rα chain. Neither anti-Tac nor RPC5 antibodies immunoprecipitated material from lysates of JAK-1 and chimeric α/γ/γ cotransfectants that was also stained by anti-JAK-1. Thus, there was no evidence that JAK-1 interacted with the cytoplasmic portion of the $\gamma_c$ receptor chain. On the other hand, when lysates from cells cotransfected with JAK-1 and chimeric α/α/β were immunoprecipitated with anti-Tac and Western blotted, material stained by anti-JAK-1 was detected.

These results established that recombinant components of the IL-2 receptor associate with each other in defined ways. Further, our results confirmed the interaction of the JAK-1 and IL-2Rβ proteins, and indicated that the cytoplasmic portion of the IL-2Rβ chain was required for this interaction.

We next used transfected COS-7 cells to evaluate the association of JAK-3 with $\gamma_c$ mutants in order to identify regions of contact between the JAK-3 and $\gamma_c$ proteins. These coprecipitation experiments employed two different anti-$\gamma_c$ antibodies, a monoclonal antibody that recognized the extracellular domain of $\gamma_c$, and R878, a polyclonal antiserum that recognized the intracellular domains of $\gamma_c$. As described below, we discovered that recombinant $\gamma_c$ and JAK-3 proteins efficiently interacted with each other. In contrast, two truncated forms of the receptor chain in which either 80 or 48 amino acids had been deleted from the C-terminus (Russell et al. *Science* 262:1880 (1993)) exhibited greatly diminished association with JAK-3. The 48 amino acid truncation is smaller than the truncation found in the XSCID patient with the smallest known naturally occurring $\gamma_c$ truncation (missing 62 amino acids). Other XSCID patients have been identified with even larger truncations. Thus, the findings presented below confirmed that the inability of JAK-3 to associate with $\gamma_c$ would be a characteristic of many XSCID patients.

Example 14 describes experiments which demonstrated recombinant $\gamma_c$ chains that incorporate mutations similar to those found in XSCID patients cannot efficiently associate with JAK-1.

EXAMPLE 14

Mutations in Recombinant $\gamma_c$ Chains Disrupt JAK-3 Binding

COS-7 cells were transfected with JAK-3 and either wild type $\gamma_c$ or $\gamma_c$-ΔCT, $\gamma_c$-ΔSH2, $\gamma_2$-L271Q or with the vector control (pME18S). The $\gamma_c$ expression construct used in these procedures is described under Example 13. The $\gamma_c$-ΔCT and $\gamma_c$-ΔSH2 constructs were prepared as described by Russell et al., in *Science* 262:1880 (1993). The $\gamma_c$-L271Q expression construct was prepared by using the pAlter-1 Mutagenesis Vector system (Promega), and is essentially identical to the wild type $\gamma_c$ construct, except for mutation of codon 271 from CTG to CAG. The transfectants were lysed and immunoprecipitated with the extracellular domain-recognizing antibody or R878 anti-$\gamma_c$ antibodies and Western blotted with JAK-3 antiserum. Expression of transfected wild type and mutant $\gamma_c$ constructs were similar as determined by flow cytometry. Note that whereas the extracellular domain-recognizing antibody mAb bound to an extracellular epitope and thereby all the mutant forms of $\gamma_c$ tested, R878 cannot bind $\gamma_c$-ΔCT or $\gamma_c$-ΔSH2 truncation mutants which lack the critical epitope.

The extracellular domain-recognizing antibody immunoprecipitates from cells cotransfected with JAK-3 and wild type $\gamma_c$ contained material that was Western blotted with anti-JAK-3. No other cotransfectant gave similar results. Repetition of the procedure using the R878 anti-$\gamma_c$ immunoprecipitates gave essentially similar results, except that a small amount of anti-JAK-3 staining material was observed in the lane corresponding to the lysate from cells that had been cotransfected with JAK-3 and $\gamma_c$-L271Q expression constructs. We noted that the amount of JAK-3 associating with $\gamma_c$-L271Q was substantially less than the amount of JAK-3 associating with the wild type $\gamma_c$. These results indicated that mutation of the amino acid at position 271 of the $\gamma_c$ chain inhibited JAK-3 binding. This implicated the region of the $\gamma_c$ protein that included amino acid position 271 as being critical for interaction with the JAK-3 protein.

Neither the vector control nor any of the $\gamma_c$ mutants that were tested in our experiments gave any indication for JAK-3 binding. Further, we discovered that the portion of the $\gamma_c$ chain that included amino acid position 271 represented a critical domain of the protein that was required for JAK-3 binding.

We have recently characterized the genetic defect in a pedigree with an X-linked combined immunodeficiency as a single nucleotide change within the $\gamma_c$ cytoplasmic domain, resulting in replacing Leu 271 with Gln. As described above, the $\gamma_c$-L271Q mutation significantly diminished but did not abrogate association with JAK-3. The finding that the $\gamma_c$-L271Q mutant still weakly associated with JAK-3 was consistent with the disease phenotype in this pedigree being less severe than typical XSCIDs. Nevertheless, affected males manifest diminished and retarded development of CD4+ and CD8+ T-cells and decreased T-cell responses to mitogens and IL-2.

Interestingly, Leu 271 is not contained within the region deleted in the $\gamma_c$-ΔSH2 mutant. We interpret this as indicating that JAK-3 may contact residues both proximal and distal to the deletion point in the $\gamma_c$-ΔSH2 construct. An experiment described in Example 15, that was conducted using a 19 amino acid long peptide spanning Leu 271, supports this hypothesis since the peptide only partially inhibited $\gamma_c$-JAK-3 coprecipitation, even when present at high molar excess. When IL-2Rβ and JAK-3 were cotransfected into COS-7 cells, Mikβ1 anti-IL-2Rβ mAb weakly but reproducibly coprecipitated JAK-3.

As described above, we have disclosed that JAK-3 is indeed the kinase that associates with $\gamma_c$ and that JAK-3 is activated and tyrosine phosphorylated by all previously known $\gamma_c$ users tested, as well as IL-9, which we now add to the list of known $\gamma_c$ users. Moreover, we have partially defined the regions and residues of $\gamma_c$ required for JAK-3 association and correlated defective $\gamma_c$-JAK-3 association with XSCID.

The activation of JAK-1 by IL-2, IL-4, IL-7, and IL-9 was an unexpected result and suggests that IL-4R, IL-7R, and IL-9R, like IL-2Rβ, all associate with JAK-1. We have recently shown that IL-15 also activates JAK-1 and JAK-3. The activation of JAK-1 and JAK-3 presumably is vital to signal transduction mediated by IL-2, IL-4, IL-7, IL-9 and IL-15. However, it is clear that the distinct signals transduced by different $\gamma_c$ users cannot be explained solely by JAK-1 and JAK-3. Unique actions, such as the induction of tyrosine phosphorylation of IRS-1 by IL-4, presumably play major roles in determining cytokine-specific actions, and may reflect the abilities of specific receptor complexes to recruit different substrates for the activated JAKs or other kinases.

Finally, we contemplate that the discoveries described above can be used to design assays for identifying compounds that inhibit IL-2 dependent signaling. Specifically, we contemplate that compounds that disrupt the interaction between JAK-1 and the IL-2Rβ subunit, or between JAK-3 and the $\gamma_c$ subunit of the IL-2 receptor will be potential inhibitors of IL-2 signalling. The descriptions provided in the foregoing Examples detail how interactions between the JAK kinases and the IL-2Rβ and $\gamma_c$ chains of the receptor can be detected. Contemplated inhibitors will be identified by virtue of inhibiting these interactions.

To illustrate how an inhibitor can be identified according to the invented method, we have conducted experiments using a synthetic peptide as a model inhibitor to inhibit the interaction between $\gamma_c$ and JAK-3 in vitro. Specifically, the peptide used in this procedure had an amino acid sequence corresponding to a portion of the $\gamma_c$ chain that binds the JAK-3 protein. The assay employed standard immunoprecipitation and Western blotting methods. In the following exemplary case, the $\gamma_c$ synthetic peptide prevented binding of wild type $\gamma_c$ to JAK-3. Since the anti-$\gamma_c$ antibody used in the immunoprecipitation procedure did not immunoprecipitate the complex between the $\gamma_c$ synthetic peptide and the JAK-3 protein, inhibition of $\gamma_c$ binding to JAK-3 was determined by virtue of the ability of the synthetic peptide to inhibit coprecipitation of the complex containing $\gamma_c$ and JAK-3. Significantly, the fact that a negative control peptide failed to inhibit the interaction between $\gamma_c$ and JAK-3 demonstrated the specificity of the inhibition. Thus, the assay described below clearly distinguished between agents that did and agents that did not inhibit the $\gamma_c$-JAK-3 interaction.

Example 15 describes an assay that can be used to identify compounds that inhibit IL-2 receptor activation by preventing the interaction between JAK-3 and the $\gamma_c$ chain.

EXAMPLE 15

An Assay for Compounds that Inhibit IL-2 Receptor Complex Formation

YT cells or COS-7 cells expressing $\gamma_c$ and JAK-3 were stimulated or not stimulated with IL-2 and then lysed with 10 mM Tris (pH 7.5) containing 2 mM EDTA, 0.15 M NaCl, 0.875% Brij 96, 0.125% NONIDET P40™, 0.4 mM sodium vanadate, 1 mM 4-(2-aminoethyl)-benzenesulfonyl fluoride hydrochloride (ICN), 2.5 mM leupeptin, 2.5 mM aprotinin. The peptide to be tested as an inhibitor corresponded to the first 19 amino acids of the $\gamma_c$ cytoplasmic tail (sequence ERTMPRIPTLKNLEDLVTE) (SEQ ID NO:7). A negative control peptide that was not expected to inhibit the interaction between $\gamma_c$ and JAK-3 corresponded to a tyrosine phosphorylated region of $\gamma_c$. The negative control peptide had the sequence APPCYTLKPET (SEQ ID NO:10), and was synthesized so that the Tyr residue at position 5 of the peptide was phosphotyrosine. The test peptide or the negative control peptide were separately added to the cell lysates to final concentrations of 140 μM. The positive control immunoprecipitation was carried out in the absence of added peptide. Lysates were immunoprecipitated for 16 hours at 4° C. using antibodies to $\gamma_c$ and protein A sepharose and washed six times before electrophoresis on SDS gels. The gels were immunoblotted with antisera to JAK-3 using ECL as described previously.

Results of the experiment described above indicated that only the competitor peptide partially inhibited $\gamma_c$-JAK-3 coprecipitation. As expected, and consistent with the findings presented under Example 12, only a weak association between the γ$_c$ and JAK-3 proteins was observed in the absence of IL-2 stimulation.

In particular, the lane corresponding to the positive control coprecipitation in the extracts from IL-2 induced cells displayed an intense band on the x-ray film at a position corresponding to a molecular weight of 125 kDa. This result indicated the position of the JAK-3 protein on the immunoblot and provided a baseline for quantitative comparison with the test and negative control samples. The lane corresponding to the negative control sample had an intensity that was essentially identical to the band intensity in the positive control lane. This result indicated that the negative control peptide failed to inhibit association of γ$_c$ and JAK-3 proteins. The lane corresponding to the sample containing the polypeptide being tested as an inhibitor had a band representing the JAK-3 protein that was of significantly diminished intensity. This result indicated that the 19 amino acid polypeptide having the sequence of SEQ ID NO:6 inhibited the γ$_c$-JAK-3 interaction. These findings illustrate the results that would be expected in assays for identifying inhibitors of the γ$_c$-JAK-3 interaction. In particular, an inhibitor of the γ$_c$-JAK-3 interaction can be identified by virtue of its ability to lessen the amount of the γ$_c$-JAK-3 coprecipitate compared to a trial that was conducted in the absence of any inhibitor.

Although the foregoing procedure was carried out by first immunoprecipitating with an anti-γ$_c$ antibody and then Western blotting and probing with an anti-JAK-3 antibody, we anticipate the order of antibody usage could be reversed with equally good results. In particular, we anticipate that immunoprecipitation could be performed using the anti-JAK-3 antibody, and the Western blot probed with the anti-γ$_c$ antibody. In this latter case, inhibitors of the γ$_c$-JAK-3 interaction would still be identified by virtue of diminishing the amount of γ$_c$-JAK-3 coprecipitate. The assay for inhibitors will involve identifying agents that cause a reduction in the amount of γ$_c$ detected on the x-ray film relative to a trial that omitted the inhibitor.

Further, we anticipate that assays such as that described under Example 15 will be useful in the discovery of non-polypeptide drugs that inhibit the γ$_c$-JAK-3 interaction. These drugs will similarly be identified in such assays by virtue of their abilities to inhibit coprecipitation of the γ$_c$-JAK-3 complex.

Still further, we contemplate coprecipitation and Western blotting assays to identify compounds that inhibit the interaction between JAK-1 or JAK-3 and IL-2Rβ. Such assays can be readily performed using techniques well known to those having ordinary skill in the art. Inhibitors of this interaction are believed useful as drugs to inhibit transmembrane signalling that is dependent on the interaction between these receptor subunits. Specifically, these drugs are anticipated for use as immunomodulators which inhibit IL-2 dependent signalling.

What is claimed is:

1. Isolated human JAK-3 protein being free of JAK-1 protein said JAK-3 protein being a protein tyrosine kinase that includes an amino acid sequence Gly-Cys-Glu-Thr-His-Ala-Phe-Thr-Ala-His-Pro-Glu-Gly-Lys-His-His-Ser-Leu-Ser-Phe-Ser (SEQ ID NO: 11), said JAK-3 protein having a molecular weight of approximately 125 kDa measurable by SDS polyacrylamide gel electrophoresis in an 8% polyacrylamide gel and Western blotting using an antibody specific for said amino acid sequence, said JAK-3 protein having tandem non-identical catalytic domains, lacking SH2 or SH3 domains, and being expressed in NK cells and stimulated or transformed T cells, but not in resting T cells, said JAK-3 protein being isolatable by immunoprecipitation with said antibody.

* * * * *

UNITED STATES PATENT AND TRADEMARK OFFICE
CERTIFICATE OF CORRECTION

PATENT NO.        : 7,070,972 B2                                                     Page 1 of 1
APPLICATION NO. : 08/373934
DATED             : July 4, 2006
INVENTOR(S)       : O'Shea et al.

It is certified that error appears in the above-identified patent and that said Letters Patent is hereby corrected as shown below:

Col. 35, Line 54 (approx.), Claim 1, after "protein" insert -- , --.

Col. 35, Line 55 (approx.), Claim 1, after "protein" insert -- , --.

Signed and Sealed this

Eighth Day of May, 2007

JON W. DUDAS
*Director of the United States Patent and Trademark Office*

SEQUENCE LISTING

```
<160> NUMBER OF SEQ ID NOS: 11

<210> SEQ ID NO 1
<211> LENGTH: 6
<212> TYPE: PRT
<213> ORGANISM: Homo Sapiens

<400> SEQUENCE: 1

Asp Val Trp Ser Phe Gly
1               5

<210> SEQ ID NO 2
<211> LENGTH: 28
<212> TYPE: DNA
<213> ORGANISM: Homo Sapiens
<220> FEATURE:
<221> NAME/KEY: misc_feature
<222> LOCATION: (1)...(28)
<223> OTHER INFORMATION: n = A,T,C or G

<400> SEQUENCE: 2
ccagcggccg cgtncaycgn gayctngc                                          28

<210> SEQ ID NO 3
<211> LENGTH: 28
<212> TYPE: DNA
<213> ORGANISM: Homo Sapiens
<220> FEATURE:
<221> NAME/KEY: misc_feature
<222> LOCATION: (1)...(28)
<223> OTHER INFORMATION: n = A,T,C or G

<400> SEQUENCE: 3
ccagcggccg cccraanswc canacrtc                                          28
```

```
<210> SEQ ID NO 4
<211> LENGTH: 6
<212> TYPE: PRT
<213> ORGANISM: Homo Sapiens
<220> FEATURE:
<221> NAME/KEY: VARIANT
<222> LOCATION: (1)...(6)
<223> OTHER INFORMATION: Xaa = Any Amino Acid

<400> SEQUENCE: 4

Gly Xaa Gly Xaa Xaa Gly
 1               5

<210> SEQ ID NO 5
<211> LENGTH: 6
<212> TYPE: PRT
<213> ORGANISM: Homo Sapiens

<400> SEQUENCE: 5

Phe Trp Tyr Ala Pro Glu
 1               5

<210> SEQ ID NO 6
<211> LENGTH: 7
<212> TYPE: PRT
<213> ORGANISM: Homo Sapiens

<400> SEQUENCE: 6

Val Asp Gly Tyr Phe Arg Leu
 1               5

<210> SEQ ID NO 7
<211> LENGTH: 19
<212> TYPE: PRT
<213> ORGANISM: Homo Sapiens

<400> SEQUENCE: 7

Glu Arg Thr Met Pro Arg Ile Pro Thr Leu Lys Asn Leu Glu Asp Leu
 1               5                  10                  15

Val Thr Glu

<210> SEQ ID NO 8
<211> LENGTH: 4064
<212> TYPE: DNA
<213> ORGANISM: Homo Sapiens
<220> FEATURE:
<221> NAME/KEY: CDS
<222> LOCATION: (96)...(3467)

<400> SEQUENCE: 8
ccctctgacc aggactgagg ggcttttct ctctgtgccc caggcaagtt gcactcatta      60
tggaattccg gcggcccgct aggcaagttg cactc atg gca cct cca agt gaa     113
                                    Met Ala Pro Pro Ser Glu
                                      1               5 gag acg ccc ctg atc cct cag cgt tca tgc agc ctc ttg tcc acg gag    161
Glu Thr Pro Leu Ile Pro Gln Arg Ser Cys Ser Leu Leu Ser Thr Glu
              10                  15                  20 gct ggt gcc ctg cat gtg ctg ctg ccc gct cgg gcc ccg ggg ccc ccc    209
Ala Gly Ala Leu His Val Leu Leu Pro Ala Arg Ala Pro Gly Pro Pro
         25                  30                  35 cag cgc cta tct ttc tcc ttt ggg gac cac ttg gct gag gac ctg tgc    257
Gln Arg Leu Ser Phe Ser Phe Gly Asp His Leu Ala Glu Asp Leu Cys
     40                  45                  50
```

-continued

| | | |
|---|---|---|
| gtg cag gct gcc aag gcc agc ggc atc ctg cct gtg tac cac tcc ctc<br>Val Gln Ala Ala Lys Ala Ser Gly Ile Leu Pro Val Tyr His Ser Leu<br>55                    60                    65                    70 | 305 |
| ttt gct ctg gcc acg gag gac ctg tcc tgc tgg ttc ccc ccg agc cac<br>Phe Ala Leu Ala Thr Glu Asp Leu Ser Cys Trp Phe Pro Pro Ser His<br>                75                    80                    85 | 353 |
| atc ttc tcc gtg gag gat gcc agc acc caa gtc ctg ctg tac agg att<br>Ile Phe Ser Val Glu Asp Ala Ser Thr Gln Val Leu Leu Tyr Arg Ile<br>          90                    95                    100 | 401 |
| cgc ttt tac ttc ccc aat tgg ttt ggg ctg gag aag tgc cac cgc ttc<br>Arg Phe Tyr Phe Pro Asn Trp Phe Gly Leu Glu Lys Cys His Arg Phe<br>              105                  110                115 | 449 |
| ggg cta cgc aag gat ttg gcc agt gct atc ctt gac ctg cca gtc ctg<br>Gly Leu Arg Lys Asp Leu Ala Ser Ala Ile Leu Asp Leu Pro Val Leu<br>120                    125                  130 | 497 |
| gag cac ctc ttt gcc cag cac cgc agt gac ctg gtg agt ggg cgc ctc<br>Glu His Leu Phe Ala Gln His Arg Ser Asp Leu Val Ser Gly Arg Leu<br>135                    140                  145                150 | 545 |
| ccc gtg ggc ctc agt ctc aag gag cag ggt gag tgt ctc agc ctg gcc<br>Pro Val Gly Leu Ser Leu Lys Glu Gln Gly Glu Cys Leu Ser Leu Ala<br>                  155                  160                165 | 593 |
| gtg ttg gac ctg gcc cgg atg gcg cga gag cag gcc cag cgg ccg gga<br>Val Leu Asp Leu Ala Arg Met Ala Arg Glu Gln Ala Gln Arg Pro Gly<br>          170                    175                  180 | 641 |
| gag ctg ctg aag act gtc agc tac aag gcc tgc cta ccc cca agc ctg<br>Glu Leu Leu Lys Thr Val Ser Tyr Lys Ala Cys Leu Pro Pro Ser Leu<br>185                    190                  195 | 689 |
| cgc gac ctg atc cag ggc ctg agc ttc gtg acg cgg agg gct att cgg<br>Arg Asp Leu Ile Gln Gly Leu Ser Phe Val Thr Arg Arg Ala Ile Arg<br>200                    205                  210 | 737 |
| agg acg gtg cgc aga gcc ctg ccg cgc gtg gcc gcc tgc cag gca gac<br>Arg Thr Val Arg Arg Ala Leu Pro Arg Val Ala Ala Cys Gln Ala Asp<br>215                    220                  225                230 | 785 |
| cgg cac tcg ctc atg gcc aag tac atc atg gac ctg gag cgg ctg gat<br>Arg His Ser Leu Met Ala Lys Tyr Ile Met Asp Leu Glu Arg Leu Asp<br>                  235                  240                245 | 833 |
| cca gcc ggg gcc gcc gag acc ttc cac gtg ggc ctc cct ggg gcc ctt<br>Pro Ala Gly Ala Ala Glu Thr Phe His Val Gly Leu Pro Gly Ala Leu<br>              250                  255                260 | 881 |
| ggt ggc cac gac ggg ctg ggg ctg ctc cgc gtg gct ggt gac ggc ggc<br>Gly Gly His Asp Gly Leu Gly Leu Leu Arg Val Ala Gly Asp Gly Gly<br>          265                    270                  275 | 929 |
| atc gcc tgg acc cag gga gaa cag gag gtc ctc cag ccc ttc tgc gac<br>Ile Ala Trp Thr Gln Gly Glu Gln Glu Val Leu Gln Pro Phe Cys Asp<br>280                    285                  290 | 977 |
| ttt cca gaa atc gta gac att agc atc aag cag gcc ccg cgc gtt ggc<br>Phe Pro Glu Ile Val Asp Ile Ser Ile Lys Gln Ala Pro Arg Val Gly<br>295                    300                  305                310 | 1025 |
| ccg gcc gga gag cac cgc ctg gtc act gtt acc agg aca gac aac cag<br>Pro Ala Gly Glu His Arg Leu Val Thr Val Thr Arg Thr Asp Asn Gln<br>                  315                  320                325 | 1073 |
| att tta gag gcc gag ttc cca ggg ctg ccc gag gct ctg tcg ttc gtg<br>Ile Leu Glu Ala Glu Phe Pro Gly Leu Pro Glu Ala Leu Ser Phe Val<br>                  330                  335                340 | 1121 |
| gcg ctc gtg gac ggc tac ttc cgg ctg acc acg gac tcc cag cac ttc<br>Ala Leu Val Asp Gly Tyr Phe Arg Leu Thr Thr Asp Ser Gln His Phe<br>          345                    350                  355 | 1169 |
| ttc tgc aag gag gtg gca ccg ccg agg ctg ctg gag gaa gtg gcc gag<br>Phe Cys Lys Glu Val Ala Pro Pro Arg Leu Leu Glu Glu Val Ala Glu<br>360                    365                  370 | 1217 |

```
cag tgc cac ggc ccc atc act ctg gac ttt gcc atc aac aag ctc aag    1265
Gln Cys His Gly Pro Ile Thr Leu Asp Phe Ala Ile Asn Lys Leu Lys
375                 380                 385                 390 act ggg ggc tca cgt cct ggc tcc tat gtt ctc cgc agc ccc cag        1313
Thr Gly Gly Ser Arg Pro Gly Ser Tyr Val Leu Arg Arg Ser Pro Gln
                395                 400                 405 gac ttt gac agc ttc ctc ctc act gtc tgt gtc cag aac ccc ctt ggt    1361
Asp Phe Asp Ser Phe Leu Leu Thr Val Cys Val Gln Asn Pro Leu Gly
            410                 415                 420 cct gat tat aag ggc tgc ctc atc cgg cgc agc ccc aca gga acc ttc    1409
Pro Asp Tyr Lys Gly Cys Leu Ile Arg Arg Ser Pro Thr Gly Thr Phe
            425                 430                 435 ctt ctg gtt ggc ctc agc cga ccc cac agc agt ctt cga gag ctc ctg    1457
Leu Leu Val Gly Leu Ser Arg Pro His Ser Ser Leu Arg Glu Leu Leu
440                 445                 450 gca acc tgc tgg gat ggg ggg ctg cac gta gat ggg gtg gca gtg acc    1505
Ala Thr Cys Trp Asp Gly Gly Leu His Val Asp Gly Val Ala Val Thr
455                 460                 465                 470 ctc act tcc tgc tgt atc ccc aga ccc aaa gaa aag tcc aac ctg atc    1553
Leu Thr Ser Cys Cys Ile Pro Arg Pro Lys Glu Lys Ser Asn Leu Ile
                475                 480                 485 gtg gtc cag aga ggt cac agc cca ccc aca tca tcc ttg gtt cag ccc    1601
Val Val Gln Arg Gly His Ser Pro Pro Thr Ser Ser Leu Val Gln Pro
            490                 495                 500 caa tcc caa tac cag ctg agt cag atg aca ttt cac aag atc cct gct    1649
Gln Ser Gln Tyr Gln Leu Ser Gln Met Thr Phe His Lys Ile Pro Ala
            505                 510                 515 gac agc ctg gag tgg cat gag aac ctg ggc cat ggg tcc ttc acc aag    1697
Asp Ser Leu Glu Trp His Glu Asn Leu Gly His Gly Ser Phe Thr Lys
520                 525                 530 att tac cgg ggc tgt cgc cat gag gtg gtg gat ggg gag gcc cga aag    1745
Ile Tyr Arg Gly Cys Arg His Glu Val Val Asp Gly Glu Ala Arg Lys
535                 540                 545                 550 aca gag gtg ctg ctg aag gtc atg gat gcc aag cac aag aac tgc atg    1793
Thr Glu Val Leu Leu Lys Val Met Asp Ala Lys His Lys Asn Cys Met
                555                 560                 565 gag tca ttc ctg gaa gca gcg agc ttg atg agc caa gtg tcg tac cgg    1841
Glu Ser Phe Leu Glu Ala Ala Ser Leu Met Ser Gln Val Ser Tyr Arg
            570                 575                 580 cat ctc gtg ctg ctc cac ggc gtg tgc atg gct gga gac agc acc atg    1889
His Leu Val Leu Leu His Gly Val Cys Met Ala Gly Asp Ser Thr Met
            585                 590                 595 gtg cag gaa ttt gta cac ctg ggg gcc ata gac atg tat ctg cga aaa    1937
Val Gln Glu Phe Val His Leu Gly Ala Ile Asp Met Tyr Leu Arg Lys
            600                 605                 610 cgt ggc cac ctg gtg cca gcc agc tgg aag ctg cag gtg gtc aaa cag    1985
Arg Gly His Leu Val Pro Ala Ser Trp Lys Leu Gln Val Val Lys Gln
615                 620                 625                 630 ctg gcc tac gcc ctc aac tat ctg gag gac aaa ggc ctg ccc cat ggc    2033
Leu Ala Tyr Ala Leu Asn Tyr Leu Glu Asp Lys Gly Leu Pro His Gly
                635                 640                 645 aat gtc tct gcc cgg aag gtg ctc ctg gct cgg gag ggg gct gat ggg    2081
Asn Val Ser Ala Arg Lys Val Leu Leu Ala Arg Glu Gly Ala Asp Gly
            650                 655                 660 agc ccg ccc ttc atc aag ctg agt gac cct ggg gtc agc ccc gct gtg    2129
Ser Pro Pro Phe Ile Lys Leu Ser Asp Pro Gly Val Ser Pro Ala Val
            665                 670                 675 tta agc ctg gag atg ctc acc gac agg atc ccc tgg gtg gcc ccc gag    2177
Leu Ser Leu Glu Met Leu Thr Asp Arg Ile Pro Trp Val Ala Pro Glu
680                 685                 690
```

-continued

```
tgt ctc cgg gag gcg cag aca ctt agc ttg gaa gct gac aag tgg ggc        2225
Cys Leu Arg Glu Ala Gln Thr Leu Ser Leu Glu Ala Asp Lys Trp Gly
695                 700                 705                 710 ttc ggc gcc acg gtc tgg gaa gtg ttt agt ggc gtc acc atg ccc atc        2273
Phe Gly Ala Thr Val Trp Glu Val Phe Ser Gly Val Thr Met Pro Ile
            715                 720                 725 agt gcc ctg gat cct gct aag aaa ctc caa ttt tat gag gac cgg cag        2321
Ser Ala Leu Asp Pro Ala Lys Lys Leu Gln Phe Tyr Glu Asp Arg Gln
730                 735                 740 cag ctg ccg gcc ccc aag tgg aca gag ctg gcc ctg ctg att caa cag        2369
Gln Leu Pro Ala Pro Lys Trp Thr Glu Leu Ala Leu Leu Ile Gln Gln
        745                 750                 755 tgc atg gcc tat gag ccg gtc cag agg ccc tcc ttc cga gcc gtc att        2417
Cys Met Ala Tyr Glu Pro Val Gln Arg Pro Ser Phe Arg Ala Val Ile
760                 765                 770 cgt gac ctc aat agc ctc atc tct tca gac tat gag ctc ctc tca gac        2465
Arg Asp Leu Asn Ser Leu Ile Ser Ser Asp Tyr Glu Leu Leu Ser Asp
775                 780                 785                 790 ccc aca cct ggt gcc ctg gca cct cgt gat ggg ctg tgg aat ggt gcc        2513
Pro Thr Pro Gly Ala Leu Ala Pro Arg Asp Gly Leu Trp Asn Gly Ala
            795                 800                 805 cag ctc tat gcc tgc caa gac ccc acg atc ttc gag gag aga cac ctc        2561
Gln Leu Tyr Ala Cys Gln Asp Pro Thr Ile Phe Glu Glu Arg His Leu
810                 815                 820 aag tac atc tca cag ctg ggc aag ggc aac ttt ggc agc gtg gag ctg        2609
Lys Tyr Ile Ser Gln Leu Gly Lys Gly Asn Phe Gly Ser Val Glu Leu
        825                 830                 835 tgc cgc tat gac ccg cta gcc cac aat aca ggt gcc ctg gtg gcc gtg        2657
Cys Arg Tyr Asp Pro Leu Ala His Asn Thr Gly Ala Leu Val Ala Val
840                 845                 850 aaa cag ctg cag cac agc ggg cca gac cag cag agg gac ttt cag cgg        2705
Lys Gln Leu Gln His Ser Gly Pro Asp Gln Gln Arg Asp Phe Gln Arg
855                 860                 865                 870 gag att cag atc ctc aaa gca ctg cac agt gat ttc att gtc aag tat        2753
Glu Ile Gln Ile Leu Lys Ala Leu His Ser Asp Phe Ile Val Lys Tyr
            875                 880                 885 cgt ggt gtc agc tat ggc ccg ggc cgg cca gag ctg cgg ctg gtc atg        2801
Arg Gly Val Ser Tyr Gly Pro Gly Arg Pro Glu Leu Arg Leu Val Met
890                 895                 900 gag tac ctg ccc agc ggc tgc ttg cgc gac ttc ctg cag cgg cac cgc        2849
Glu Tyr Leu Pro Ser Gly Cys Leu Arg Asp Phe Leu Gln Arg His Arg
        905                 910                 915 gcg cgc ctc gat gcc agc cgc ctc ctt ctc tat tcc tcg cag atc tgc        2897
Ala Arg Leu Asp Ala Ser Arg Leu Leu Leu Tyr Ser Ser Gln Ile Cys
920                 925                 930 aag ggc atg gag tac ctg ggc tcc cgc cgc tgc gtg cac cgc gac ctg        2945
Lys Gly Met Glu Tyr Leu Gly Ser Arg Arg Cys Val His Arg Asp Leu
935                 940                 945                 950 gcc gcc cga aac atc ctc gtg gag agc gag gca cac gtc aag atc gct        2993
Ala Ala Arg Asn Ile Leu Val Glu Ser Glu Ala His Val Lys Ile Ala
            955                 960                 965 gac ttc ggc cta gct aag ctg ctg ccg ctt gac aaa gac tac tac gtg        3041
Asp Phe Gly Leu Ala Lys Leu Leu Pro Leu Asp Lys Asp Tyr Tyr Val
970                 975                 980 gtc cgc gag cca ggc cag agc ccc att ttc tgg tat gcc ccc gaa tcc        3089
Val Arg Glu Pro Gly Gln Ser Pro Ile Phe Trp Tyr Ala Pro Glu Ser
        985                 990                 995 ctc tcg gac aac atc ttc tct cgc cag tca gac gtc tgg agc ttc ggg        3137
Leu Ser Asp Asn Ile Phe Ser Arg Gln Ser Asp Val Trp Ser Phe Gly
1000                1005                1010
```

-continued

| | | | | | | | | | | | | | | | |
|---|---|---|---|---|---|---|---|---|---|---|---|---|---|---|---|
| gtc | gtc | ctg | tac | gag | ctc | ttc | acc | tac | tgc | gac | aaa | agc | tgc | agc | ccc | 3185
| Val | Val | Leu | Tyr | Glu | Leu | Phe | Thr | Tyr | Cys | Asp | Lys | Ser | Cys | Ser | Pro |
| 1015 | | | | 1020 | | | | 1025 | | | | 1030 | | | |

| tcg | gcc | gag | ttc | ctg | cgg | atg | atg | gga | tgt | gag | cgg | gat | gtc | ccc | gcc | 3233
| Ser | Ala | Glu | Phe | Leu | Arg | Met | Met | Gly | Cys | Glu | Arg | Asp | Val | Pro | Ala |
| | | | | 1035 | | | | 1040 | | | | 1045 | | | |

| ctc | tgc | cgc | ctc | ttg | gaa | ctg | ctg | gag | gag | ggc | cag | agg | ctg | ccg | gcg | 3281
| Leu | Cys | Arg | Leu | Leu | Glu | Leu | Leu | Glu | Glu | Gly | Gln | Arg | Leu | Pro | Ala |
| 1050 | | | | 1055 | | | | 1060 | | | | | | | |

| cct | cct | gcc | tgc | cct | gct | gag | gtt | cac | gag | ctc | atg | aag | ctg | tgc | tgg | 3329
| Pro | Pro | Ala | Cys | Pro | Ala | Glu | Val | His | Glu | Leu | Met | Lys | Leu | Cys | Trp |
| 1065 | | | | 1070 | | | | 1075 | | | | | | | |

| gcc | cct | agc | cca | cag | gac | cgg | cca | tca | ttc | agc | gcc | ctg | ggc | ccc | cag | 3377
| Ala | Pro | Ser | Pro | Gln | Asp | Arg | Pro | Ser | Phe | Ser | Ala | Leu | Gly | Pro | Gln |
| 1080 | | | | 1085 | | | | 1090 | | | | | | | |

| ctg | gac | atg | ctg | tgg | agc | gga | agc | cgg | ggg | tgt | gag | act | cat | gcc | ttc | 3425
| Leu | Asp | Met | Leu | Trp | Ser | Gly | Ser | Arg | Gly | Cys | Glu | Thr | His | Ala | Phe |
| 1095 | | | | 1100 | | | | 1105 | | | | 1110 | | | |

| act | gct | cac | cca | gag | ggc | aaa | cac | cac | tcc | ctg | tcc | ttt | tca | | | 3467
| Thr | Ala | His | Pro | Glu | Gly | Lys | His | His | Ser | Leu | Ser | Phe | Ser | | |
| | | | | 1115 | | | | 1120 | | | | | | | |

```
tagctcctgc ccgcagacct ctggattagg tctctgttga ctggctgtgt gaccttaggc      3527
ccggagctgc ccctctctgg gcctcagagg cctttatgagg gtcctctact tcaggaacac    3587
ccccatgaca ttgcatttgg ggggctcccc gtggcctgta aatagcctg tggcctttgc      3647
aatttgttaa ggttcaagac agatgggcat atgtgtcagt ggggctctct gagtcctggc      3707
ccaaagaagc aaggaaccaa atttaagact ctcgcatctt cccaacccct taagccctgg    3767
ccccctgagt ttcctttctc cgtctctctc ttttttatttt ttttatttt atttttattt    3827
ttgagacaga gcctcgctcg ttacccaggg tggagtgcag tggtagcgat ctcggctcac      3887
agtgcaacct ctgcttccca ggttcaagcg attctcctgc ctcagcctcc cgagtagctg    3947
ggattacagg tgtgcaccac cacacccggc taatttttttt tatttttaat agagatgagg    4007
tttcaccatg atggccaggc tgatctcgaa ctcctaacct caagtgatcc tcccacc       4064
```

<210> SEQ ID NO 9
<211> LENGTH: 1124
<212> TYPE: PRT
<213> ORGANISM: Homo Sapiens

<400> SEQUENCE: 9

| Met | Ala | Pro | Pro | Ser | Glu | Glu | Thr | Pro | Leu | Ile | Pro | Gln | Arg | Ser | Cys |
|---|---|---|---|---|---|---|---|---|---|---|---|---|---|---|---|
| 1 | | | | 5 | | | | | 10 | | | | | 15 | |

| Ser | Leu | Leu | Ser | Thr | Glu | Ala | Gly | Ala | Leu | His | Val | Leu | Leu | Pro | Ala |
| | | | 20 | | | | | 25 | | | | | 30 | | |

| Arg | Ala | Pro | Gly | Pro | Pro | Gln | Arg | Leu | Ser | Phe | Ser | Phe | Gly | Asp | His |
| | | 35 | | | | | 40 | | | | | 45 | | | |

| Leu | Ala | Glu | Asp | Leu | Cys | Val | Gln | Ala | Ala | Lys | Ala | Ser | Gly | Ile | Leu |
| | 50 | | | | | 55 | | | | | 60 | | | | |

| Pro | Val | Tyr | His | Ser | Leu | Phe | Ala | Leu | Ala | Thr | Glu | Asp | Leu | Ser | Cys |
| 65 | | | | | 70 | | | | | 75 | | | | | 80 |

| Trp | Phe | Pro | Pro | Ser | His | Ile | Phe | Ser | Val | Glu | Asp | Ala | Ser | Thr | Gln |
| | | | | 85 | | | | | 90 | | | | | 95 | |

| Val | Leu | Leu | Tyr | Arg | Ile | Arg | Phe | Tyr | Phe | Pro | Asn | Trp | Phe | Gly | Leu |
| | | | 100 | | | | | 105 | | | | | 110 | | |

| Glu | Lys | Cys | His | Arg | Phe | Gly | Leu | Arg | Lys | Asp | Leu | Ala | Ser | Ala | Ile |
| | | 115 | | | | | 120 | | | | | 125 | | | |

-continued

```
Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
                180                 185                 190

Cys Leu Pro Pro Ser Leu Arg Asp Leu Ile Gln Gly Leu Ser Phe Val
                195                 200                 205

Thr Arg Arg Ala Ile Arg Arg Thr Val Arg Arg Ala Leu Pro Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
                260                 265                 270

Val Ala Gly Asp Gly Gly Ile Ala Trp Thr Gln Gly Glu Gln Glu Val
            275                 280                 285

Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Pro Arg Leu
                355                 360                 365

Leu Glu Glu Val Ala Glu Gln Cys His Gly Pro Ile Thr Leu Asp Phe
    370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
                420                 425                 430

Ser Pro Thr Gly Thr Phe Leu Leu Val Gly Leu Ser Arg Pro His Ser
                435                 440                 445

Ser Leu Arg Glu Leu Leu Ala Thr Cys Trp Asp Gly Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
                500                 505                 510

Phe His Lys Ile Pro Ala Asp Ser Leu Glu Trp His Glu Asn Leu Gly
                515                 520                 525

His Gly Ser Phe Thr Lys Ile Tyr Arg Gly Cys Arg His Glu Val Val
    530                 535                 540
```

-continued

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
            565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
    610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
    690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
        755                 760                 765

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Ala His Asn Thr
        835                 840                 845

Gly Ala Leu Val Ala Val Lys Gln Leu Gln His Ser Gly Pro Asp Gln
    850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Pro
                885                 890                 895

Glu Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
        915                 920                 925

Tyr Ser Ser Gln Ile Cys Lys Gly Met Glu Tyr Leu Gly Ser Arg Arg
    930                 935                 940

Cys Val His Arg Asp Leu Ala Ala Arg Asn Ile Leu Val Glu Ser Glu
945                 950                 955                 960

```
Ala His Val Lys Ile Ala Asp Phe Gly Leu Ala Lys Leu Leu Pro Leu
            965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
            995                1000                1005

Asp Val Trp Ser Phe Gly Val Val Leu Tyr Glu Leu Phe Thr Tyr Cys
       1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
            1045                1050                1055

Gly Gln Arg Leu Pro Ala Pro Pro Ala Cys Pro Ala Glu Val His Glu
            1060                1065                1070

Leu Met Lys Leu Cys Trp Ala Pro Ser Pro Gln Asp Arg Pro Ser Phe
            1075                1080                1085

Ser Ala Leu Gly Pro Gln Leu Asp Met Leu Trp Ser Gly Ser Arg Gly
            1090                1095                1100

Cys Glu Thr His Ala Phe Thr Ala His Pro Glu Gly Lys His His Ser
1105                1110                1115                1120

Leu Ser Phe Ser

<210> SEQ ID NO 10
<211> LENGTH: 11
<212> TYPE: PRT
<213> ORGANISM: Homo Sapiens
<220> FEATURE:
<221> NAME/KEY: PHOSPHORYLATION
<222> LOCATION: 5

<400> SEQUENCE: 10

Ala Pro Pro Cys Tyr Thr Leu Lys Pro Glu Thr
1               5                   10

<210> SEQ ID NO 11
<211> LENGTH: 21
<212> TYPE: PRT
<213> ORGANISM: Homo sapiens

<400> SEQUENCE: 11

Gly Cys Glu Thr His Ala Phe Thr Ala His Pro Glu Gly Lys His His
1               5                   10                  15

Ser Leu Ser Phe Ser
            20
```